United States Patent [19]

Orlowski et al.

[11] 4,427,799
[45] Jan. 24, 1984

[54] DENTAL RESTORING MATERIAL AND A FILLER THEREFOR

[75] Inventors: Jan A. Orlowski, Altadena; David V. Butler, West Covina, both of Calif.

[73] Assignee: Blendax-Werke R. Schneider GmbH & Co., Mainz, Fed. Rep. of Germany

[21] Appl. No.: 304,647

[22] Filed: Sep. 23, 1981

[30] Foreign Application Priority Data

Mar. 24, 1981 [EP] European Pat. Off. ........ 81102198.9

[51] Int. Cl.³ .......................... C08L 33/10; C08K 3/36
[52] U.S. Cl. .................................... 523/116; 523/117; 523/212; 523/213; 523/220; 433/212; 433/228
[58] Field of Search ............... 523/116, 117, 212, 213, 523/220; 433/228, 212

[56] References Cited

U.S. PATENT DOCUMENTS

| | | | |
|---|---|---|---|
| 2,859,198 | 11/1958 | Sears et al. | 523/212 |
| 3,649,588 | 3/1972 | Kennedy-Skipton | 523/212 |
| 3,808,170 | 4/1974 | Rogers | 523/466 |
| 4,297,266 | 10/1981 | Ibsen et al. | 523/117 |
| 4,302,376 | 11/1981 | Walkowiak et al. | 523/177 |

*Primary Examiner*—Lewis T. Jacobs
*Attorney, Agent, or Firm*—Connolly and Hutz

[57] ABSTRACT

Dental restoring materials on the basis of polymerizable compounds which show good mechanical properties and satisfactory polishability after hardening containing at least one new filler consisting preferably of porous silica with a medium particle size from about 5 to about 300 millimicrons and an organo-silicon content from about 5 to about 25%, preferably from 10-12 to 18-20%.

8 Claims, No Drawings

DENTAL RESTORING MATERIAL AND A FILLER THEREFOR

The present invention relates to a new filler for dental restoring materials on the basis of polymerizable compounds and dental restoring materials containing such a filler.

Dental restoring materials on the basis of compounds which may be hardened by polymerization, so-called "composites", contain, besides one or more polymerizable monomers, polymerization catalysts, accelerators, UV-stabilizers etc., obligatorily a mineral filler compound.

Principally there are existing two different kinds of fillers: So-called "macrofillers", i.e., fillers with a medium particle diameter of more than 0.5 microns, preferably 1–2 microns, up to about 70, preferably about 50 microns. Such fillers are contained in "composite" materials in a quantity of about 60 to about 80% by weight of the total composition. The higher the share of filler, the better the physical properties of the polymerized material; the higher the share of "macrofiller", the worse, however, the polishability of the polymerized (cured) filling, too.

To improve the polishability of such fillings it has, therefore, been already suggested to develop fillers with smaller particle sizes to be inserted in dental restoring materials which give a certain polishability to the cured filling.

The German Accepted Patent Specification Nos. 2,403,211 and 2,405,576 disclose the application of inorganic fillers, particularly silica, with average particle sizes from about 5 to about 700 millimicrons in dental restoring materials.

The improvement of the polishability by use of these fillers will be, however, accompanied by a decrease of the physical properties, particularly of the water sorption of the filling as these "microfillers" with a medium particle diameter from about 10 to about 300 millimicrons may only be incorporated into the dental restoring material with a share from about 15 to about 50% by weight; i.e., the resin:filler ratio in the restoring material may be 1:1 at the maximum. Normally, silanized porous silicon dioxides with a degree of silanization due to a maximum organosilicon content of 2.5% by weight are used as "microfillers".

It has already been proposed to insert mixtures of "macrofillers", i.e. fillers with a medium particle size from about 1 to about 40 microns and "microfillers", i.e. fillers with a medium particle size from about 10 to about 300 millimicrons in dental restoring materials.

Thus, the German Published Patent Application No. 2,705,220 discloses dental filling materials containing a mixture of 70 to 95% by weight of a particle size from 0.7 to 25 microns and 5 to 30% by weight with a particle size from 0.2 to 0.7 microns.

In fact, such filling materials show an improved polishability, but their water sorption is unacceptably high.

It has now been found that dental restoring materials with satisfactory polishability can be prepared by maintaining their good physical properties, particularly a low water sorption value, by use of an inorganic material, especially porous silica, with a medium particle diameter from about 5 to about 300 millimicrons, which is silanized in such a way that its organosilicon content amounts from about 5 to about 25, preferably from about 8 to about 20, particularly from about 10 to 12 to about 18% (calculated on the filler).

Surprisingly, with such a filler it is possible to reach a filler:resin ratio up to 6.3:1, which exceeds considerably the values known up to now.

A filling material with especially impressive physical properties will be obtained by use of a composition containing about 50 to about 88% by weight, calculated on the total composition, of a filler containing from 8, particularly 12, to about 60% by weight of at least one silanized inorganic filler, especially a porous silica, with a medium particle diameter from about 5 to about 300 millimicrons, and an organosilicon content between about 5 and about 25%, and 40 to 92% by weight of at least one preferably non-porous filler with a medium particle size of at least about 0.5 microns together with at least one polymerizable monomer and with other usual components customary in dental restoratives.

A filling produced with such a material shows optimal properties, particularly with regard to its polishability, hardness, tensile strength and water sorption.

As already stated, the filler which is applied as a "microfiller" according to the invention is preferably a porous silicon dioxide.

The silanization of this material to obtain the high organosilicon content may be effected with every appropriate organosilane of the general formula

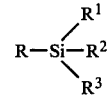

wherein R, $R^1$, $R^2$ and $R^3$ represent the same or different organic groups provided that at least one group is an OH group or at least one group which may be transferred to an OH-group, e.g. by hydrolysis, particularly an alkoxy group. Preferred organosilicons are (meth) acroyl propyl dihydroxymethoxy silane, (meth) acroyl propyl hydroxydimethoxy silane, (meth) acroyl propyl trimethoxysilane, or their mixtures. Vinyl triethoxy silane or vinyl tri (methoxyethoxy) silane are also appropriate silanization compounds. The organosilicon content of the filler is understood as the amount of organosilane which is bound to the filler. According to a preferred embodiment of the invention where a "macrofiller" is used in admixture with the "microfiller" having an organosilicon content between 5 and 25%, said "microfiller" may be any radiolucent or X-ray opaque filler which has been suggested for this purpose, and which may possibly be also silanized in a common way, whereas the maximum organosilicon content in this respect is about 2.5% by weight, calculated on the "macrofiller".

Appropriate "macrofillers" are the various silica modifications like glass in form of powdered glass, glass fibers, quartzite, christobalite, etc. for radiolucent compositions and barium aluminium silicate, barium aluminium borate silicate, lithium aluminium silicate, or glass ceramic materials for X-ray opaque compositions. Suitable X-ray opaque fillers are, e.g., disclosed in U.S. Pat. Nos. 3,801,344, 3,808,170, and 3,975,203 as well as in German Published Patent Application No. 2,347,591.

A summary of appropriate filler materials is given by R. L. Bowen, Journal of Dental Research, Vol. 58/5 (May 1979), page 1493 to 1501, especially 1495 to 1498.

Principally, all appropriate compounds suggested for this purpose may be applied as polymerizable monomers in the dental restoring material according to the invention. In this respect, the common reaction products from Bisphenol are especially suitable, particularly from Bisphenol A and glycidyl methacrylate known as Bis-GMA, the various diol dimethacrylates such as 1,6-hexanediol dimethacrylate, 1,4-butanediol dimethacrylate, tri- or tetraethyleneglyeol dimethacrylate, bis-(2-methacroyl propyl)-phthalate, -isophthalate or -terephthalate, trimethylolpropanedi- and trimethacrylate, the reaction products from diisocyanates and hydroxyalkylmethacrylates, as described, e.g., in German Published Patent Application No. 2,312,599, adducts from (di) isocyanates and 2,2-propanebis-(3-(4-phenoxy)-1,2-hydroxypropane-1-methacrylate) according to U.S. Pat. No. 3,629,187, the adducts from isocyanates and methacryloyl alkyl ethers, -alkoxy benzenes, and -alkoxy cycloalkanes, resp., as they are described in the European Patent Application No. 80 10 43 11.8 of the inventors.

Of course, also mixtures of appropriate monomers may be used.

The dental restoring materials containing the fillers according to the invention are applied in two modifications; either as self-curing preparations kept in two separate phases from which the one phase contains a polymerization initiator, e.g. a peroxide, and the other phase contains an accelerator for this peroxide, e.g. an amine, whereas both phases are brought together directly before the tooth filling and polymerization takes place in the opened cavity to be filled and which preferably has been treated with a liner shortly before restoration.

It is, however, also possible to produce one-phase preparations which polymerize under the influence of light, e.g. visible light, U.V. rays or laser light, which must contain a photo-polymerization initiator and optionally also an accelerator therefor.

Suitable photo-polymerization initiators are well-known, preferably carbonyl compounds such as benzoin and its derivatives, particularly benzoin methyl ether, benzil and benzil derivatives, e.g. 4,4-oxydibenzil or other dicarbonyl compounds, e.g. diacetyl, 2,3-pentanedione or metal carbonyls, quinone or its derivatives. The amount of photo-polymerization initiator is about 0.01 to about 5% by weight of the total composition.

These photo-polymerizable preparations preferably contain so-called polymerization accelerators. These are substances which accelerate the polymerization reaction in the presence of polymerization initiators. Common accelerators are, e.g., amines such as p-toluidine, dimethyl-p-toluidine, trialkyl amines, e.g. trihexyl amine, polyamines such as N,N,N',N'-tetraalkyl alkylenediamines, barbituric acid, dialkyl barbituric acids, and sulfimides, preferably in a quantity of about 0.01 to about 5% by weight of the total composition.

If the dental restoring material containing the filler with an organosilicon content from about 5 to about 25% according to the invention is not light-curing but kept in two separate phases until its application, one of these mixtures normally contains a polymerization initiator.

Usually this is a peroxide which decomposes at the beginning of the polymerization reaction under radical formation. Appropriate peroxides are, e.g., aryl peroxides such as benzoyl peroxide, cumol hydroperoxide, urea peroxide, butyl hydroperoxide or perbenzoate and silyl peroxides, preferably in quantities from about 0.01 to about 5, particularly about 0.5 to 2.5% by weight of the total composition.

If one phase of the two-phases compositions contains a polymerization initiator, it is suitable to add an accelerator of the above-described type, preferably an amine or barbituric acid or their derivatives, e.g. a dialkyl barbituric acid, to the other phase.

It is advisable to add UV-stabilizers to dental restoring materials based on synthetic resins to avoid darkening during the aging of the fillings.

A particular appropriate UV-stabilizer is 2-hydroxy-4-methoxybenzophenone. A further preferred material is 2-(2-hydroxy-5-methylphenyl)benzotriazole; in principle, however, each physiological inert agent absorbing UV-rays is suitable for this purpose. Other suitable compounds are hydroquinone, p-benzoquinone, p-butyl hydroxytoluene, etc. The last-mentioned compound also acts as an antioxidant in the filling.

A review on the substances which are usually applied in dental restoring materials is given in the article of R. L. Bowen in Journal of Dental Research, Vol. 58/5 (May 1979), pages 1493 to 1503, as well as in the Supplement by J. F. Lann, pages 1504 to 1506, whose disclosure is included herein.

In order to adjust an impression of the filled tooth surfaces as natural as possible composite materials contain, if necessary, also a small amount of dyes or pigments.

The following examples shall explain the invention, but give no limitation of the claims.

EXAMPLE A

Preparation of a highly silanized filler with a particle size between 10 and 50 millimicrons 200 g methacroyl propyl trimethoxysilane, 3 g acetic acid and 350 g deionized water are mixed together within 30 minutes at room temperature. To this mixture 2000 g acetone are added and then 1000 g microporous silica with a medium particle size from 10 to 50 millimicrons and a specific surface of 60 m$^2$/g are added stepwise.

The obtained paste is dried at 50° C. and pressed through a 325 Mesh sieve to yield 1150 g of a fine white powder with a pH-value of 8.

EXAMPLE 1

| Light-curing restoring material | |
|---|---|
| Reaction product of Bisphenol A and glycidyl methacrylate (Bis-GMA) | 25 (parts by weight) |
| Methylene-4,4',N,N'—bis-p-toluylene carbamate of 3-methacroyl-2-hydroxypropoxy benzene | 25 |
| Silanized SiO$_2$ (10% organosilicon; medium particle diameter ~30-50 millimicrons) | 15 |
| Barium silicate (2% organosilicon; medium particle diameter ~2-10 microns) | 170 |
| Pyrogenic SiO$_2$ (Aerosil ®) | 1,5 |
| Benzil | 1 |
| Trihexyl amine | 1,8 |
| Optionally traces of dye | |

After polymerization a product with the following properties was obtained:
Diametral tensile strength: 8,050 psi
Water sorption: 0.43 mg/cm$^2$ Barcol hardness (after one hour): 96°–97°
Compressive strength: 26,000 psi
Polishability with Shofu tool: good

EXAMPLE 2

| Light-curing restoring material | |
|---|---|
| Bis-GMA | 25 (parts by weight) |
| Methylene-4,4',N,N'—biscyclohexyl carbamate of 3-methacroyl-2-hydroxy-propoxytoluene | 30 |
| Tetraethyleneglycol dimethacrylate | 20 |
| 1,6-hexanediol dimethacrylate | 10 |
| Silanized SiO$_2$ (12% organosilicon; medium particle diameter ~10–50 millimicrons) | 57,7 |
| Barium aluminium silicate (2% organosilicon; medium particle diameter ~10 microns) | 563 |
| Pyrogenic SiO$_2$ (e.g. Aerosil ®) | 5 |
| 4,4-oxydibenzil | 0,3 |
| Dimethyl-p-toluidine | 0,5 |
| Optionally traces of pigments | |

Properties of the cured product:
Diametral tensile strength: 8,190 psi
Water sorption: 0.366 mg/cm$^2$
Barcol hardness (7 days/37° C.): 98°–99°
Compressive strength: 30,000 psi
Polishability with Shofu tool: well

EXAMPLE 3

| Two-phase restoring material Composition: | A | B |
|---|---|---|
| 2,2-Bis-(4'-(3"-methacroyl-2"-hydroxy propoxy)phenyl)propane (Bis-GMA) | 12 | 12 |
| 2,2-Bis-(4'-(2"-methacroylethoxy)-phenyl)propane (EBA) | 66 | 66 |
| Triethyleneglyeol dimethacrylate | 22 | 22 |
| Tertiary butylhydroxytoluol (BHT) | 0,03 | 0,15 |
| UV-absorber | 0,6 | 0,6 |
| Benzoyl peroxide | | 2,0 |
| N,N—(2-hydroxyethyl)-p-toluidine | 3,6 | |
| Ferrous oxide pigment | 0,02 | |
| Filler, produced according to example A | 135 | 135 |
| | (parts by weight) | |

After curing at 23° C. a product with the following properties was obtained:
Hardness (Barcol): 96
Diametral tensile strength: 5,000 psi (357 kg/cm$^2$)
Polishability: excellent

EXAMPLE 4

| Two-phase restoring material Composition: | A | B |
|---|---|---|
| Bis-GMA | 12 | |
| EBA | 66 | |
| Triethyleneglycol dimethacrylate | 22 | |
| Hexanediol dimethacrylate | | 28 |
| Methylene-4,4',N,N'—biscyclohexyl-carbamate of 3-methacroyl-2-hydroxy-propoxybenzene (urethane methacrylate) | | 72 |
| UV-absorber | 0,6 | 0,6 |
| BHT | 0,03 | 0,15 |
| Dimethyl-p-toluidine | 3,5 | |
| Benzoyl peroxide | | 2,2 |
| Glass ceramic filler according to Accepted German Patent Application No. 2,347,591 (particle size from 1 to 10 microns) | 125 | 125 |
| Filler, produced according to example A | 80 | 60 |

| Two-phase restoring material Composition: | A | B |
|---|---|---|
| | | (parts by weight) |

Properties of the product after polymerization at 23° C.:
Hardness (Barcol): 97
Diametral tensile strength: 5,700 psi (404 kg/cm$^2$)
Polishability: well

EXAMPLE 5

| Two-phase restoring material Composition: | A | B |
|---|---|---|
| Bis-GMA | 12 | |
| EBA | 66 | |
| Triethyleneglycol dimethacrylate | 22 | |
| Hexanediol dimethacrylate | | 30 |
| Urethane methacrylate | | 70 |
| UV-absorber | 0,6 | 0,6 |
| Diethyl-p-toluidine | 3,6 | |
| BHT | 0,03 | 0,15 |
| Cumol hydroperoxide | | 2,2 |
| Ferrous oxide pigment | 0,02 | |
| Filler, produced according to example A | 94 | 94 |
| Corning ® glass 7724 (quartz); medium particle size 2 microns; 100% < 40 microns | 750 | 550 |
| | (parts by weight) | |

Properties of the polymer cured at 23° C.:
Hardness (Barcol): 99
Diametral tensile strength: 7,200 psi (510 kg/cm$^2$)
Polishability: well

EXAMPLE 6

| Two-phase restoring material Composition: | A | B |
|---|---|---|
| Bis-GMA | 12 | |
| EBA | 66 | |
| Triethyleneglycol dimethacrylate | 22 | |
| Hexanediol dimethacrylate | | 30 |
| Urethane methacrylate | | 70 |
| UV-absorber | 0,6 | 0,6 |
| Diethyl barbituric acid | 3,6 | |
| BHT | 0,03 | 0,15 |
| Benzoyl peroxide | | 2,2 |
| Dye | 0,02 | |
| Lanthanum silicate glass filler (below 10 microns; medium particle diameter 0,50 to 1 micron) | 350 | 300 |
| Filler, prepared according to example A | 30 | 30 |
| | (parts by weight) | |

Properties of the product obtained after curing at 13° C.:
Hardness (Barcol): 98
Diametral tensile strength: 6,200 psi (440 kg/cm$^2$)
Polishability: well

EXAMPLE 7

| Two-phase restoring material Composition: | A | B |
|---|---|---|
| Bis-GMA | 10 | 12 |
| EBA | 60 | 66 |
| Triethyleneglycol dimethacrylate | 22 | 22 |
| UV-absorber | 0,6 | 0,6 |
| Diethyl barbituric acid | 3,6 | |

-continued

| Two-phase restoring material Composition: | A | B |
|---|---|---|
| BHT | 0,03 | 0,15 |
| Benzoyl peroxide |  | 2,2 |
| Dye | 0,02 |  |
| Corning ® 7740 borosilicate-glass (below 40 microns; medium particle diameter 2 microns) | 200 | 200 |
| Filler, produced according to example A | 50 | 45 |
|  | (parts by weight) | |

After curing at 23° C. a product with the following properties was obtained:

Hardness (Barcol): 97
Diametral tensile strength: 5,600 psi (397 kg/cm$^2$)
Polishability: well

We claim:

1. Dental restoring material comprising about 50 to about 88% by weight, calculated on the total composition, of a filler and at least one polymerizable compound, characterized in that the filler is a mixture of
   (a) 8 to 60% by weight of at least one silanized filler with a medium particle diameter from about 5 to about 300 millimicrons and an organosilicon content from about 5 to about 25%, calculated on the total filler, and
   (b) 40 to 92% by weight of at least one filler with a medium particle diameter of at least about 0.5 microns.

2. Dental restoring material according to claim 1, characterized by the fact that the filler (b) with a medium particle diameter of at least 0.5 microns is a nonporous filler.

3. Dental restoring material according to claim 1 or 2, characterized by the fact that the filler (b) has been silanized.

4. Dental restoring material claim 1 characterized by the fact that the filler (a) has a medium particle diameter from about 10 to about 100 millimicrons.

5. Dental restoring material claim 1 characterized by the fact that the silanized filler (a) has an organosilicon content from about 10 to about 20% (calculated to the total filler).

6. In a dental restoring material containing a polymerizable component and a filler component, wherein the improvement comprises as a filler component a silanized material with a medium particle diameter from about 5 to about 300 millimicrons and an organosilicon content from about 5 to 25% based on the silanized material.

7. The dental restoring material according to claim 6 wherein said silanized material is silanized porous silica.

8. In the process of restoring damaged teeth by applying a dental restoring material to the damaged teeth, the improvement comprises said dental restoring material containing a material according to claim 6.

* * * * *